United States Patent
Roy

(10) Patent No.: US 12,329,889 B2
(45) Date of Patent: Jun. 17, 2025

(54) REDUCING SORBENT CARTRIDGE RECHARGING REQUIREMENTS

(71) Applicant: Mozarc Medical US LLC, Minneapolis, MN (US)

(72) Inventor: Arindam G. Roy, Bangalore, IN (US)

(73) Assignee: Mozarc Medical US LLC, Minneapolis, MN (US)

( * ) Notice: Subject to any disclaimer, the term of this patent is extended or adjusted under 35 U.S.C. 154(b) by 365 days.

(21) Appl. No.: 17/306,214

(22) Filed: May 3, 2021

(65) Prior Publication Data
US 2022/0347361 A1    Nov. 3, 2022

(51) Int. Cl.
*A61M 1/16* (2006.01)
*B01J 20/02* (2006.01)
*B01J 20/06* (2006.01)
*B01J 20/32* (2006.01)

(52) U.S. Cl.
CPC ........ *A61M 1/1696* (2013.01); *A61M 1/1601* (2014.02); *B01J 20/0211* (2013.01); *B01J 20/0292* (2013.01); *B01J 20/06* (2013.01); *B01J 20/3236* (2013.01); *A61M 2205/0205* (2013.01); *A61M 2205/60* (2013.01); *B01J 2220/62* (2013.01)

(58) Field of Classification Search
CPC .............. A61M 1/1601; A61M 1/1696; A61M 2202/203; A61M 2205/0205; A61M 2205/60; A61M 2205/6018; B01J 20/0211; B01J 20/0292; B01J 20/06; B01J 20/3236; B01J 2220/62
See application file for complete search history.

(56) References Cited

U.S. PATENT DOCUMENTS

| | | |
|---|---|---|
| 2013/0199998 A1 | 8/2013 | Kelly |
| 2015/0238673 A1* | 8/2015 | Gerber ................. G06K 19/077 210/85 |
| 2015/0250937 A1* | 9/2015 | Pudil ................... A61M 1/1696 210/264 |

FOREIGN PATENT DOCUMENTS

| | | |
|---|---|---|
| WO | 1994029228 | 12/1994 |
| WO | 2015199863 | 12/2015 |

* cited by examiner

*Primary Examiner* — Dirk R Bass

(57) ABSTRACT

Systems and methods for reducing the burden of recharging on patients and caregivers are provided. The systems and methods use a microbe removal layer upstream of a sorbent cartridge in a sorbent-based dialysis system. The systems and methods can determine whether the bacterial content and remaining capacity of a non-recharged sorbent module are suitable for the sorbent module to be reused safely and effectively without recharging.

19 Claims, 6 Drawing Sheets

REDUCING SORBENT CARTRIDGE RECHARGING REQUIREMENTS

FIELD

The invention relates to systems and methods for reducing a burden of recharging a sorbent cartridge on patients and caregivers. The systems, compositions, and methods use a microbe removal layer upstream of a sorbent cartridge in a sorbent-based dialysis system. The systems and methods can determine whether the bacterial content and remaining capacity of a non-recharged sorbent module allow for the sorbent module to be reused without recharging safely and effectively.

BACKGROUND

Sorbent based dialysis systems commonly use zirconium phosphate and zirconium oxide to remove solutes from spent dialysate. To reduce costs, the zirconium phosphate and zirconium oxide can be recharged, restoring the capacity of the sorbent materials, and disinfecting the sorbent cartridge. The most widely used form of home dialysis involves short "daily" home hemodialysis sessions for 2 to 5 hours, 5 to 7 times a week. Recharging the sorbent materials after every dialysis session can place a large burden on the patient or caregiver. Notably, conventional sorbent modules are typically designed for longer in-clinic dialysis sessions. However, an ion exchanging capacity of zirconium phosphate or zirconium oxide in a reusable sorbent module may not be completely exhausted if the volume of spent dialysate volume passed through the sorbent cartridge is less than the spent dialysate volume allowed to pass in a conventional hemodialysis treatment session of 4-5 hours. A multiuse sorbent cartridge or sorbent module may be used for more than one session without a recharge if there is remaining capacity and microbe growth in the cartridge is under control. Conventional approaches fail to recapture unspent capacity. Hence, there is a need for systems and methods for determining a remaining capacity of a sorbent cartridge or sorbent module after a dialysis session. There is a further need for systems and methods to limit bacterial entry to the sorbent cartridge to control microbe growth. The need extends to systems and methods to determine whether a sorbent cartridge or sorbent module used in a prior dialysis session can be reused safely and effectively.

SUMMARY OF THE INVENTION

The problem to be solved by the present invention is to reduce the burden on patients and caregivers of recharging sorbent modules after every dialysis session. The solution is to include a microbe removal layer upstream of the sorbent modules to reduce the bacterial growth inside the sorbent module and to reuse the sorbent module if the remaining capacity allows.

The first aspect of the invention relates to a system. In any embodiment, the system can include at least a first sorbent module, the first sorbent module containing at least zirconium oxide and/or zirconium phosphate; and a microbe removal layer upstream of the zirconium oxide and/or zirconium phosphate.

In any embodiment, the microbe removal layer can be in a second sorbent module.

In any embodiment, the microbe removal layer can be either silver impregnated activated carbon or a halide resin and silver impregnated activated carbon.

In any embodiment, the first sorbent module can contain zirconium oxide.

In any embodiment, the first sorbent module can contain zirconium phosphate.

In any embodiment, the system can include an identification component affixed to or embedded in the first sorbent module.

In any embodiment, the identification component can be an RFID component.

In any embodiment, the system can include a control system; the control system programmed to determine whether the first sorbent module is usable in a present dialysis session based on data from the identification component.

In any embodiment, the control system can be programmed to determine that the first module is usable if a remaining capacity of the first module is above a preset value and either of: (a) the first sorbent module has not been used in a dialysis session since a last recharge; or (b) the first sorbent module has been used in a prior dialysis session since a last recharge and the prior dialysis session was within a preset length of time of the present dialysis session.

In any embodiment, the preset length of time can be about 36 hours.

In any embodiment, the remaining capacity of the first sorbent module can be determined based on a volume of dialysate passed through the first sorbent module in the prior dialysis session.

The features disclosed as being part of the first aspect of the invention can be in the first aspect of the invention, either alone or in combination, or follow any arrangement or permutation of any one or more of the described elements. Similarly, any features disclosed as being part of the first aspect of the invention can be in a second aspect of the invention described below, either alone or in combination, or follow any arrangement or permutation of any one or more of the described elements.

The second aspect of the invention relates to a method. In any embodiment, the method can include the step of determining whether a first sorbent module containing zirconium oxide and/or zirconium phosphate is useable in a present dialysis session; wherein the first sorbent module was used in a prior dialysis session; and wherein during the prior dialysis session, a microbe removal layer was upstream of the zirconium oxide and/or zirconium phosphate.

In any embodiment, the first sorbent module can be determined to be useable if a remaining capacity of the first module is above a preset value and if either (a) the first sorbent module has not been used in a dialysis session since a last recharge; or (b) the first sorbent module has been used in a prior dialysis session since a last recharge and the prior dialysis session was within a preset length of time of the present dialysis session.

In any embodiment, data used to determine whether the first sorbent module is usable can be obtained from an identification component affixed to or embedded in the first sorbent module.

In any embodiment, the microbe removal layer can be either silver impregnated activated carbon or a halide resin and silver impregnated activated carbon.

In any embodiment, the first sorbent module can contain zirconium oxide.

In any embodiment, the first sorbent module can contain zirconium phosphate.

In any embodiment, the microbe removal layer could have been in a second sorbent module.

In any embodiment, the step of determining whether the first sorbent module is usable can be performed by a control system of a dialysis system.

In any embodiment, the method can include the step of performing dialysis with the first sorbent module if the first sorbent module is determined to be usable.

The features disclosed as being part of the second aspect of the invention can be in the second aspect of the invention, either alone or in combination, or follow any arrangement or permutation of any one or more of the described elements. Similarly, any features disclosed as being part of the second aspect of the invention can be in the first aspect of the invention, either alone or in combination, or follow any arrangement or permutation of any one or more of the described elements.

DETAILED DESCRIPTION

Figure 1:
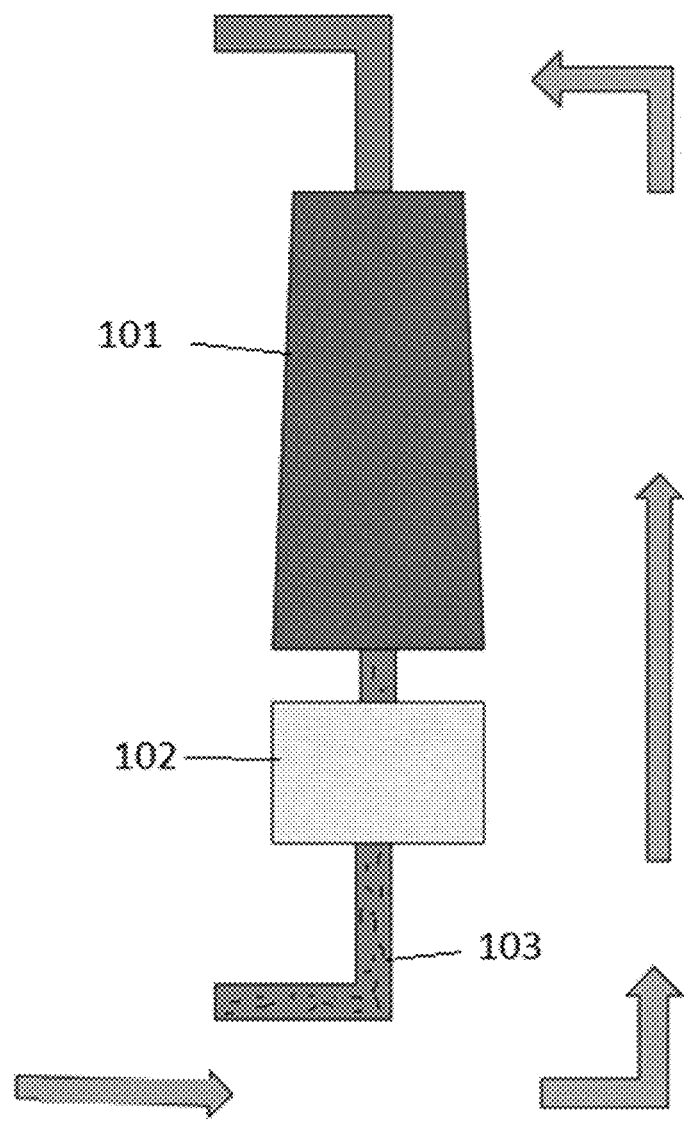
FIG. 1 is an illustration of a portion of a dialysate flow path.

Unless defined otherwise, all technical and scientific terms used have the same meaning as commonly understood by one of ordinary skill in the art.

The articles "a" and "an" are used to refer to one to over one (i.e., to at least one) of the grammatical object of the article. For example, "an element" means one element or over one element.

"Activated carbon" refers to a form of carbon processed to have small pores, increasing the surface area available for adsorption.

The term "affixed" refers to a component being physically attached to a second component or system.

The term "comprising" includes, but is not limited to, whatever follows the word "comprising." Use of the term indicates the listed elements are required or mandatory but that other elements are optional and may be present.

The term "consisting of" includes and is limited to whatever follows the phrase "consisting of." The phrase indicates the limited elements are required or mandatory and that no other elements may be present.

The term "consisting essentially of" includes whatever follows the term "consisting essentially of" and additional elements, structures, acts, or features that do not affect the basic operation of the apparatus, structure or method described.

The term "containing" or to "contain" refers to a substance that is within a component or container.

A "control system" can be a combination of components that act together to maintain a system to a desired set of performance specifications. The control system can use processors, memory and computer components configured to interoperate to maintain the desired performance specifications. The control system can also include fluid or gas control components, and solute control components as known within the art to maintain performance specifications.

The term "data" refers to any information concerning a given person, component, process, or system.

The terms "determining" or to "determine" refer to ascertaining a particular state of a component or system.

A "dialysis session" can be any time period of any length during which a patient is treated by or undergoes dialysis, hemodialysis, hemofiltration, ultrafiltration, or other fluid removal therapy.

The term "dialysis system" refers to a set of components used to perform a dialysis session.

The term "embedded in" refers to a component being within the structure of a second component.

The terms "first," "second," and "third," and the like, refer to separate and distinct features. For example, one or more sections can be identified as a 'first section," "second section," and "third section." Alternatively, one or more diameters can be identified as a 'first diameter," "second diameter," and "third diameter."

The term "fluidly connectable" refers to the ability of providing for the passage of fluid, gas, or combination thereof, from one point to another point. The ability of providing such passage can be any connection, fastening, or forming between two points to permit the flow of fluid, gas, or combinations thereof. The two points can be within or between any one or more of compartments of any type, modules, systems, components, and rechargers.

The term "fluidly connected" refers to a particular state such that the passage of fluid, gas, or combination thereof, is provided from one point to another point. The connection state can also include an unconnected state, such that the two points are disconnected from each other to discontinue flow. It will be further understood that the two "fluidly connectable" points, as defined above, can form a "fluidly connected" state. The two points can be within or between any one or more of compartments, modules, systems, components, and rechargers, all of any type.

A "halide resin" is a polymer having at least one halogen atom per monomer.

An "identification component" is a component that allows for identification of and information about a particular component to which the identification component is attached.

The term "last recharge" refers to the immediately preceding instance of a sorbent material being recharged.

A "microbe removal layer" is a layer of material that can remove, kill, or otherwise destroy the viability of microbes.

The term "passed through" refers to a fluid moving into and out of a component or system.

The term "performing" or to "perform" refers to the process of carrying out an action or method.

The term "present dialysis session" refers to a dialysis session that is ongoing or to begin.

A "preset length of time" refers to a duration of time determined prior to a process.

A "preset value" refers to a value for a given parameter determined prior to a process.

A "prior dialysis session" is a dialysis session that has already occurred.

The term "programmed," when referring to a processor or control system, can mean a series of instructions that cause a processor or control system to perform certain steps.

"Radio Frequency Identification" or "RFID component" refers to a device, component, or electrical circuit of any type capable of transmitting, receiving, or both transmitting or receiving passively or actively, radio frequency signals to and from a receiver.

The term "recharge" or "recharging" refers to treating a sorbent material to restore the functional capacity of the sorbent material to put the sorbent material back into a condition for reuse or use in a new dialysis session. In some instances, the total mass, weight and/or amount of "rechargeable" sorbent materials remain the same. In some instances, the total mass, weight and/or amount of "rechargeable" sorbent materials change. Without being limited to any one theory of invention, the recharging process may involve exchanging ions bound to the sorbent material with different ions, which in some instances may increase or decrease the total mass of the system. However, the total amount of the sorbent material will in some instances be unchanged by the recharging process. Upon a sorbent material undergoing "recharging," the sorbent material can then be said to be "recharged."

The term "remaining capacity" refers to the ability of an exchange resin to continue removing specified solutes from a solution.

The term "silver impregnated activated carbon" refers to porous activated carbon having silver particles finely distributed on internal surfaces of the activated carbon.

The term "sorbent cartridge" refers to a cartridge containing one or more sorbent materials for removing specific solutes from solution. The term "sorbent cartridge" does not require the contents in the cartridge be sorbent based, and the contents of the sorbent cartridge can be any contents capable of removing solutes from a dialysate. The sorbent cartridge may include any suitable amount of one or more sorbent materials. In certain instances, the term "sorbent cartridge" refers to a cartridge which includes one or more sorbent materials besides one or more other materials capable of removing solutes from dialysate. "Sorbent cartridge" can include configurations where at least some materials in the cartridge do not act by mechanisms of adsorption or absorption.

A "sorbent module" or "sorbent cartridge module" means a discreet component of a sorbent cartridge. Multiple sorbent cartridge modules can be fitted together to form a sorbent cartridge of two, three, or more sorbent cartridge modules. The "sorbent cartridge module" or "sorbent module" can contain any selected materials for use in sorbent dialysis and may or may not contain a "sorbent material" or adsorbent, but less than the full complement of sorbent materials needed. In other words, the "sorbent cartridge module" or "sorbent module" generally refers to the use of the "sorbent cartridge module" or "sorbent module" in sorbent-based dialysis, e.g., REDY (REcirculating DYalysis), and not that a "sorbent material" that is necessarily contained in the "sorbent cartridge module" or "sorbent module."

The term "upstream" can refer to a position of a first component in a flow path relative to a second component wherein fluid will pass by the first component prior to the second component during normal operation. The first component can be said to be "upstream" of the second component, while the second component is "downstream" of the first component.

The term "usable" refers to the ability for a component to be used in a specified operation without significant modification.

The term "volume of dialysate" refers to a measure of the amount of fluid used during a dialysis session.

Zirconium oxide" is a sorbent material that removes anions from a fluid, exchanging the removed anions for different anions.

"Zirconium phosphate" is a sorbent material that removes cations from a fluid, exchanging the removed cations for different cations.

Sorbent Cartridge for Reduced Recharging Requirements

FIG. 1 illustrates a portion of a dialysis flow path 101 usable to reduce the recharging requirements of a sorbent cartridge 102. During dialysis, toxins and other impurities can cross from the blood of the patient into the dialysate through a dialyzer membrane (not shown). The impurities and waste products can be removed from the spent dialysate by a sorbent cartridge 102. In addition to removing waste species from the spent dialysate, the sorbent cartridge 102 can act as a microbial filter, trapping endotoxins and bacteria from the spent dialysate. Activated carbon and activated alumina in the sorbent cartridge 102 can remove endotoxins and reduce bacterial count. Packed powered beds of zirconium phosphate and zirconium oxide also trap bacteria and microbes. Fluid exiting the sorbent cartridge 102 can have a bacterial count of <1 cfu/mL and a detectable endotoxin amount of 0.3 EU/mL, both approaching the levels required of ultrapure water. If the sorbent cartridge 102 were to be reused without disinfection, unacceptably high levels of bacteria may be present.

To reduce the level of bacteria and endotoxins entering sorbent cartridge 102, a microbe removal layer 103 can be positioned upstream of the sorbent cartridge 102. The microbe removal layer can remove or destroy bacteria. Reducing the bacteria count entering the sorbent cartridge 102 will also reduce endotoxin formation, as endotoxins are also continuously released during bacterial cell growth and cell division. The spent dialysate in the dialysate flow path 101 can be pumped through the microbe removal layer 103 prior to entering sorbent cartridge 102, reducing the bacteria count entering sorbent cartridge 102.

The microbe removal layer 103 serves to reduce the viable bacteria count. In certain embodiments, the microbial removal layer 103 can include a layer of silver impregnated activated carbon. Alternatively, the microbial removal layer 103 can include a halide resin and silver impregnated activated carbon. Although shown as a separate module upstream of the sorbent cartridge 102 in FIG. 1, the microbe removal layer 103 can be positioned in the same sorbent column with the other sorbent materials. Silver ions can bind to the bacterial cell wall blocking transport of substances in and out of the cell. Further, silver ions are transported into the bacterial cell whereby the silver ions block the respiratory system and destroy the energy production of the bacteria. The silver ions can result in the bacterial cell membrane bursting, and destruction of the bacteria. Silver ions in solution provide multiple sites of antimicrobial action on target cells. Using the microbe removal layer 103 reduces the likelihood of microbes and colony forming units entering any reusable sorbent modules.

Figure 2:
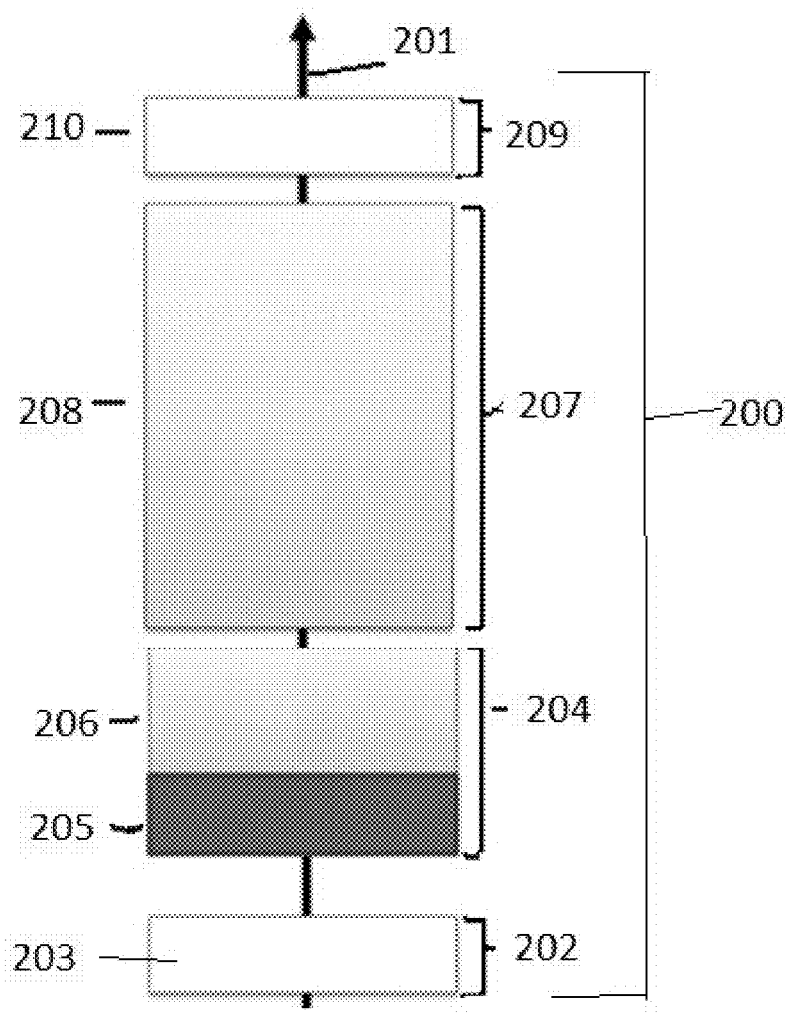
FIG. 2 is a diagram of a sorbent cartridge.

FIG. 2 is a schematic of a non-limiting embodiment of a modular sorbent cartridge 200 that can be used as described. Fluid in a dialysate flow path 201 can enter the sorbent cartridge 200 into a first sorbent module 202. The first sorbent module 202 can contain a microbe removal layer 203. As described, the microbe removal layer 203 can include silver impregnated activated carbon, or alternatively a halide resin and silver impregnated activated carbon. The microbe removal layer 203 removes bacteria and endotoxins from the spent dialysate, limiting the number of bacteria and endotoxins that reach the other sorbent modules. The activated carbon in microbe removal layer 203 can also remove nonionic toxins from the fluid by adsorption. Creatinine, glucose, uric acid, β2-macroglobulin and other non-ionic toxins, except urea, can be adsorbed onto the activated carbon, removing those toxins from the fluid.

After passing through the first sorbent module 202, the spent dialysate can enter second sorbent module 204. The second sorbent module 204 can include an additional layer of activated carbon 205 and a layer of alumina and urease 206. The second layer of activated carbon 205 can remove any remaining non-ionic toxins. Although shown as having two layers of activated carbon in FIG. 2, the sorbent cartridge 200 can use a single layer of silver impregnated activated carbon or halide resin and silver impregnated activated carbon without the second layer of activated carbon 205. The alumina in the layer of alumina and urease 206 supports the urease enzyme. Urease catalyzes the reaction of urea to form ammonium ions and carbon dioxide.

After passing through the second sorbent module 204, spent dialysate can enter a third sorbent module 207. Third sorbent module 207 can contain zirconium phosphate layer 208. In the zirconium phosphate layer 208, ammonium, calcium, potassium, and magnesium cations can be exchanged for sodium and hydrogen cations.

After passing through third sorbent module 207, the spent dialysate can enter a fourth sorbent module 209. The fourth sorbent module 209 can include zirconium oxide layer 210. The zirconium oxide layer 210 can remove phosphate and fluoride anions. Fluid exiting sorbent cartridge 200 can then be reused as dialysate, after addition of ions such as bicarbonate, calcium, potassium, and magnesium.

One of skill in the art will understand that the arrangement of modules and materials illustrated in FIG. 2 is for illustrative purposes only. Alternative arrangements can be used, so long as a layer of zirconium phosphate is downstream of the urease and the microbe removal layer is upstream of the sorbent materials to be recharged. For example, the microbe removal layer can be placed in the same sorbent module as the urease and alumina. Alternatively, the zirconium phosphate and/or zirconium oxide can be placed in the same sorbent module as the activated carbon and/or alumina and urease. In certain embodiments, one or more of the sorbent materials can be mixed into a single layer. Additionally, any number of sorbent modules can be used, including 2, 3, 4, 5, or more sorbent modules, each containing the same or different sorbent materials. The individual sorbent modules can connect directly through one or more connectors. Alternatively, the sorbent modules can be separated, with fluid lines between any of the sorbent modules.

Silver impregnated activated carbon can have a carbonaceous adsorbent with silver finely distributed on the internal surface. Introduction of a small amount of silver onto the surface of carbon can inhibit the growth and reproduction of bacteria. One of skill in the art will understand that several methods exist for generating a silver impregnated activated carbon. As a non-limiting example, activated carbon can be washed with an aqueous solution of silver nitrate and sodium borohydride. Alternatively, activated carbon can be treated with other aqueous solutions of silver salts, such as silver lactate or silver citrate. As an alternative example, a silver halide solution in ammonia can be agitated with a fine fog of activated carbon in a reactor. Additional methods for generating silver impregnated activated carbon exist and can be used for the invention. In addition, a halide resin may be included with the silver impregnated activated carbon. Halide resins, such as polyvinyl halide and poly(vinylpyridinium halide), have also been shown to remove bacteria from water. Addition of a halide resin to the silver impregnated activated carbon may increase the efficiency of bacteria removal. Other antibacterial halide resins are known in the art and can be used.

After use, one or more of the sorbent modules can be recharged to restore the capacity of the sorbent material and allow for reuse of the sorbent module. For example, a zirconium phosphate sorbent module can be recharged by flowing a solution containing sodium and hydrogen ions through the sorbent module. A zirconium oxide sorbent module can be recharged by flowing an aqueous basic solution through the sorbent module. During recharging, the sorbent modules are also disinfected.

As described, when used by most patients for a short at home dialysis session, the zirconium phosphate and zirconium oxide sorbents materials do not reach capacity. As such, recharging of the sorbent materials can be avoided if bacterial growth can be limited. Reusing the sorbent modules without recharging after every dialysis session reduces the burden on the user.

In certain embodiments, a dialysis system can include a control system that can determine whether a specified sorbent module is in condition for reuse. The reusable sorbent modules, such as a sorbent module containing zirconium oxide or zirconium phosphate, can be equipped with an identification component that will allow the control system to determine whether the sorbent module is in condition for use. To be in condition for reuse, the remaining capacity of the sorbent module should be high enough for a subsequent dialysis session and the bacterial count in the sorbent module should be low enough for safe use. Generally, if a microbe removal layer is positioned upstream of the sorbent module during treatment, the bacterial count in the sorbent module will remain low enough for safe use for at least 36 hours.

Figure 3A:
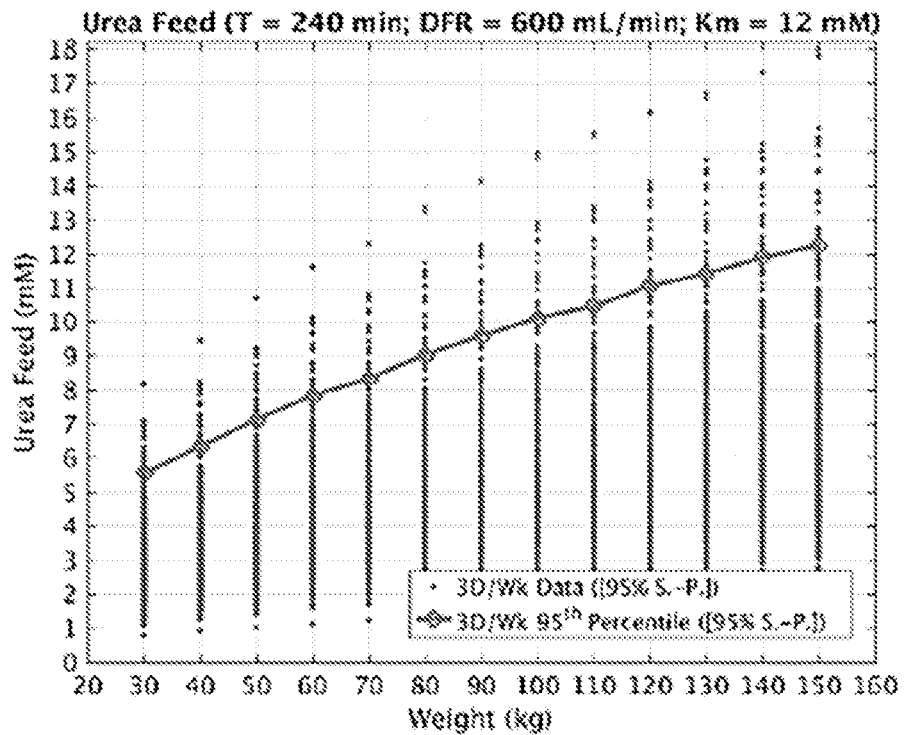
FIGS. 3A-3D are graphs showing time-averaged feed amounts of solutes as a function of patient weight.
Figure 3B:
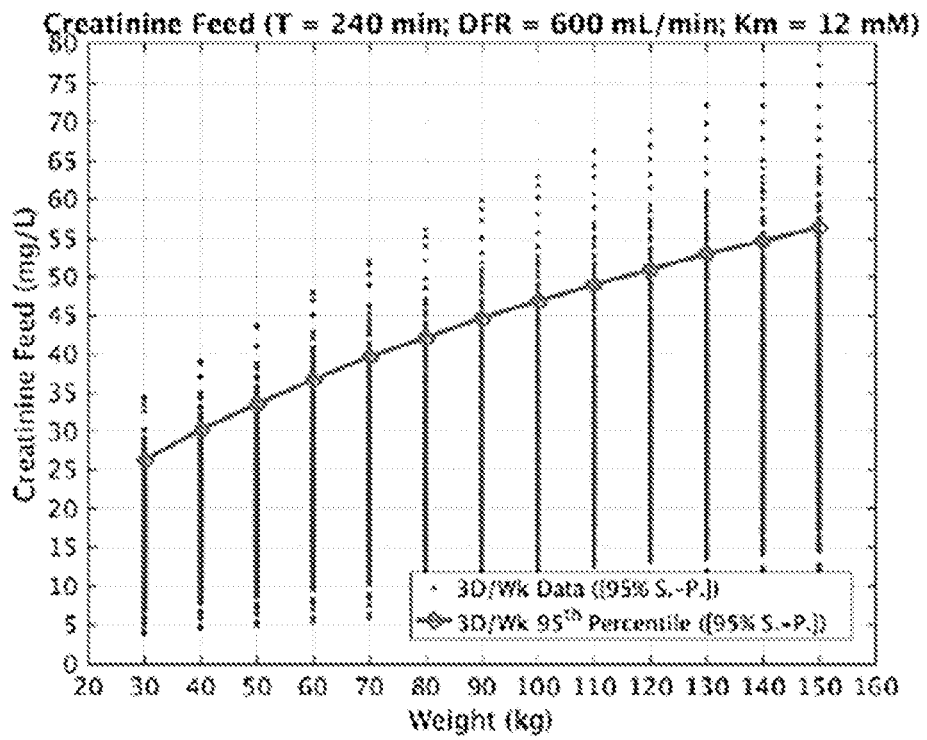
Figure 3C:
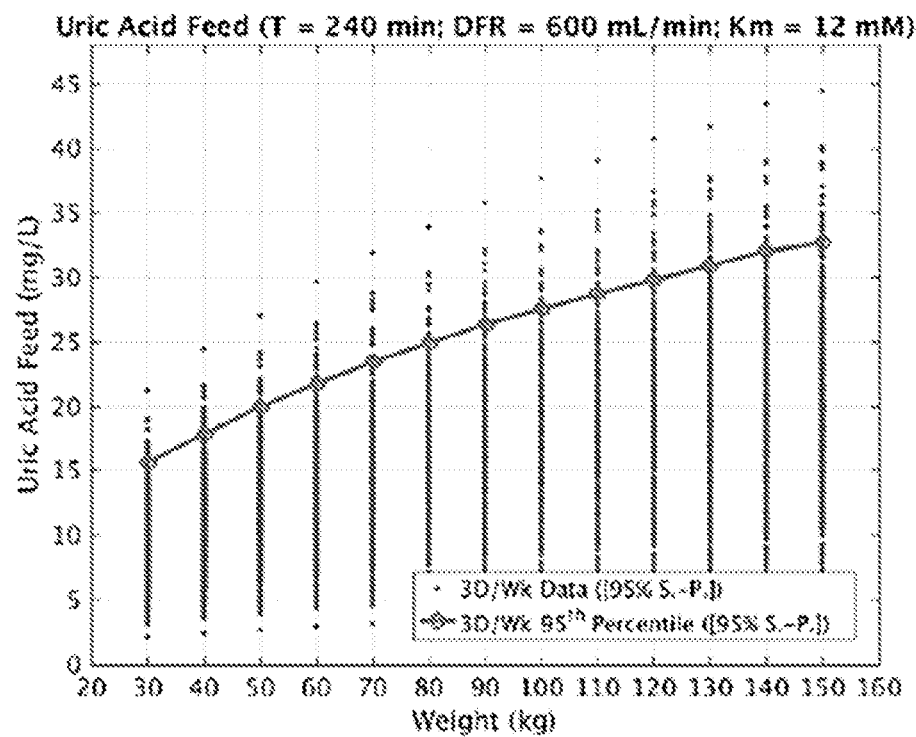
Figure 3D:
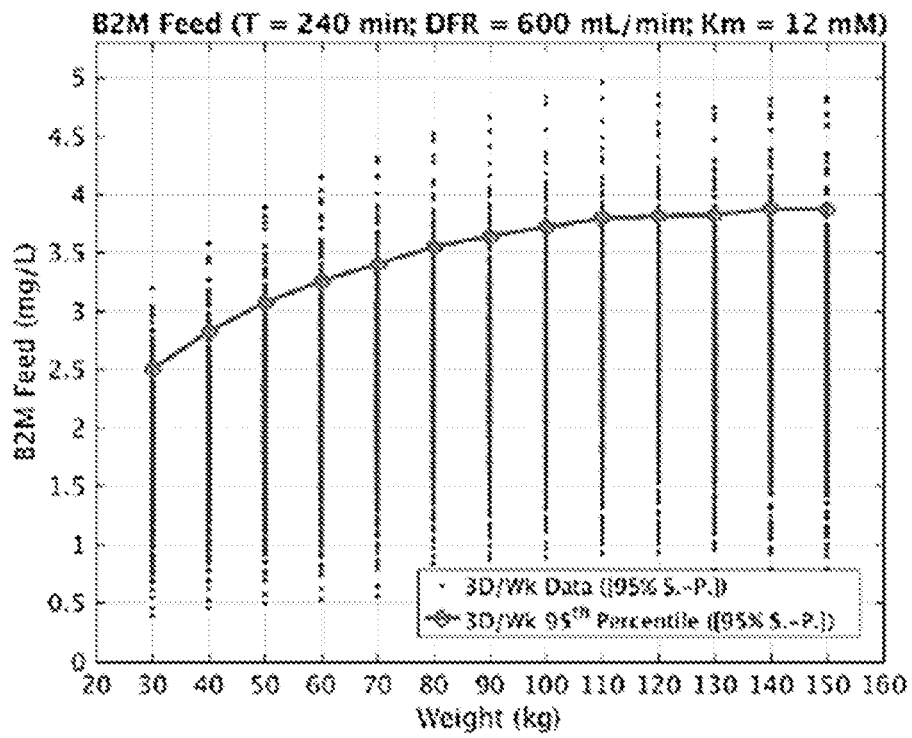

FIGS. 3A-D are graphs showing the time-averaged feed amounts into a sorbent cartridge during treatment as a function of patient weight. In each of FIGS. 3A-D, the graph was made assuming a 240-minute dialysis session and a dialysate flow rate of 600 mL/min. The Michaelis constant for the urease used was 12 mM. FIG. 3A illustrates the urea feed into the sorbent cartridge, FIG. 3B illustrates the creatinine feed into the sorbent cartridge, FIG. 3C illustrates the uric acid feed into the sorbent cartridge, and FIG. 3D illustrates the β-2 macroglobulin feed into the sorbent cartridge. The solid line in FIGS. 3A-D shows the $95^{th}$ percentile of the time-averaged sorbent cartridge feed for each solute.

As illustrated in FIG. 3A, the amount of urea fed into the sorbent cartridge increases with increasing weight of the patient. For light-weight patients, such as about a 30 kg patient, the time average urea feed is about 5.5 mM. As the patient weight increases, the amount of urea fed into the sorbent cartridge increases, to about 12.2 mM for a 150 kg patient.

Similarly, as shown in FIG. 3B, the creatinine feed increases from about 26 mg/L for a 30 kg patient to about 56 mg/L for a 150 kg patient. The uric acid feed shown in FIG. 3C increases from about 16 mg/L for a 30 kg patient to about 32 mg/L for a 150 kg patient. The β-2 macroglobulin feed increases from about 2.5 mg/L for a 30 kg patient to about 3.9 mg/L for a 150 kg patient. For all the solutes shown in FIGS. 3A-D, the time-averaged feed amount of the solute increases with increasing patient weight.

As described, urease in the sorbent cartridge catalyzes the reaction of urea to ammonium ions and carbon dioxide. The ammonium ions are then adsorbed by the zirconium phosphate. Ammonium ions are adsorbed by the zirconium phosphate efficiently up to the point where the capacity of the zirconium phosphate is exceeded. Because the time-averaged feed amount of urea is related to patient weight, the amount of ammonium ions adsorbed by the zirconium phosphate is also related to patient weight. As such, the remaining capacity of a sorbent module containing zirconium phosphate after a dialysis session is a function of the starting capacity and the patient weight.

In certain embodiments, the system can use different sized sorbent cartridges depending on patient weight. For example, a patient weighing between 30-70 kg could use a first size, a patient weighing between 70-110 kg can use a second size, and a patient weighing more than 110 kg can use a third size. Irrespective of the size of the sorbent cartridge, a limit may be placed on the volume of dialysate passed through the sorbent cartridge because the sorbent cartridge must be designed to regenerate the dialysate on every pass through the sorbent cartridge. The larger the volume of dialysate passed through the cartridge, the larger the sorbent capacity would have to be to accommodate that volume.

The volume of dialysate passed through the sorbent cartridge can be obtained through mathematical modeling. The volume of dialysate passed through the sorbent cartridge affects the dialysate flow rates and dialysis time achievable on the hemodialysis system. For any combination of dialysate flow rate and dialysis session time, the volume passed through the sorbent cartridge can be limited to a maximum volume. The two most important predictors for determination of column capacity were found to be BUN level in the patient and volume or size of the patient.

For example, a 100 kg man may use on average 120 L of dialysate during a conventional 4-5 hours 3 times/week hemodialysis session. If only 60 L dialysate is used in a session, then the sorbent cartridge capacity is not fully utilized. Based on the volume of spent dialysate and the quality of source water, the control system may be able to calculate the capacity utilized of the sorbent cartridge used, and thereby determine the remaining capacity of each sorbent module. Based on the remaining capacity, the control system may allow reuse of the sorbent modules without recharging, if the dialysate flow rate and dialysis time for the session leads to a spent dialysate volume through the sorbent modules that is less than the remaining capacity, and if microbial growth is limited.

In certain embodiments, the volume of spent dialysate flowed through a sorbent module can be tracked by an identification component. The identification component can be affixed to the sorbent module, or alternatively embedded in the sorbent module or sorbent material. The dialysate flow rate and session time, or alternatively the volume of dialysate used, can be stored on the identification component after a dialysis session. The system can read the identification component and determine the remaining capacity of the sorbent material based on the volume of spent dialysate flowed through the sorbent module. The identification component can also store the time or date of the previous dialysis session and the last recharge of the sorbent module. Any identification component that can store information can be used. In certain embodiments, the identification component can be an RFID card. The dialysis system can store information on the RFID card during or after a dialysis system. Prior to a subsequent dialysis session, the system can read the information from the RFID card to determine whether the sorbent module is usable. Alternative identification components, such as a bar code, Bluetooth communication device, or any other component can be used.

Figure 4:
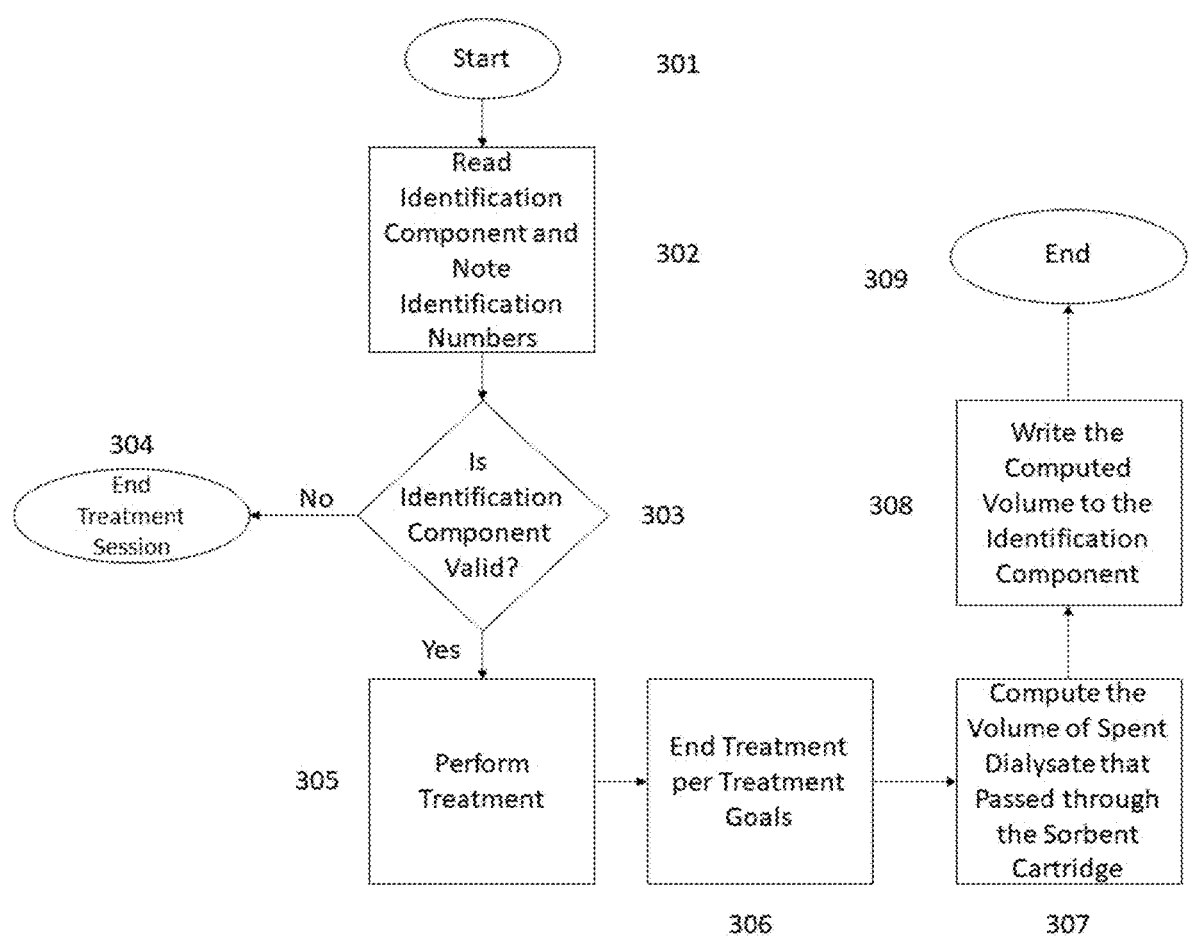
FIG. 4 is a flow chart illustrating a method of using a sorbent module for the first time.

FIG. 4 is a flow chart showing the method for using a sorbent module for the first time. The same method can be used for the first use of a sorbent module after recharging the sorbent module. The method can start in step 301. In step 302, the system can read the identification component affixed to, or embedded in, each sorbent module. In step 303, the system can determine whether the identification component is valid. An invalid identification component could mean that the component should not be used, or that the component is a counterfeit component. If the identification component is found invalid, the treatment session can end immediately in step 304. If the identification component is found to be valid, dialysis treatment can begin in step 305. Treatment can be performed by the system until the dialysis session ends in step 306. As described, the length of time of the dialysis session can depend on the system capabilities and treatment goals. In step 307, the system can optionally compute the volume of spent dialysate that passed through the sorbent cartridge during the dialysis session. The volume can be written to the identification component of each reusable sorbent module in step 308. Alternatively, the data used to compute the volume of dialysate passed through the sorbent cartridge can be written to the identification component, and the volume computed prior to a subsequent dialysis session. As described the volume of dialysate passed through the sorbent cartridge can be determined from the length of the dialysis session and the dialysate flow rate used. The volume of dialysate passed through the sorbent cartridge can be used to determine or estimate the remaining capacity of the sorbent modules. The method can end in step 309, with the reusable sorbent modules either stored or recharged.

Figure 5:
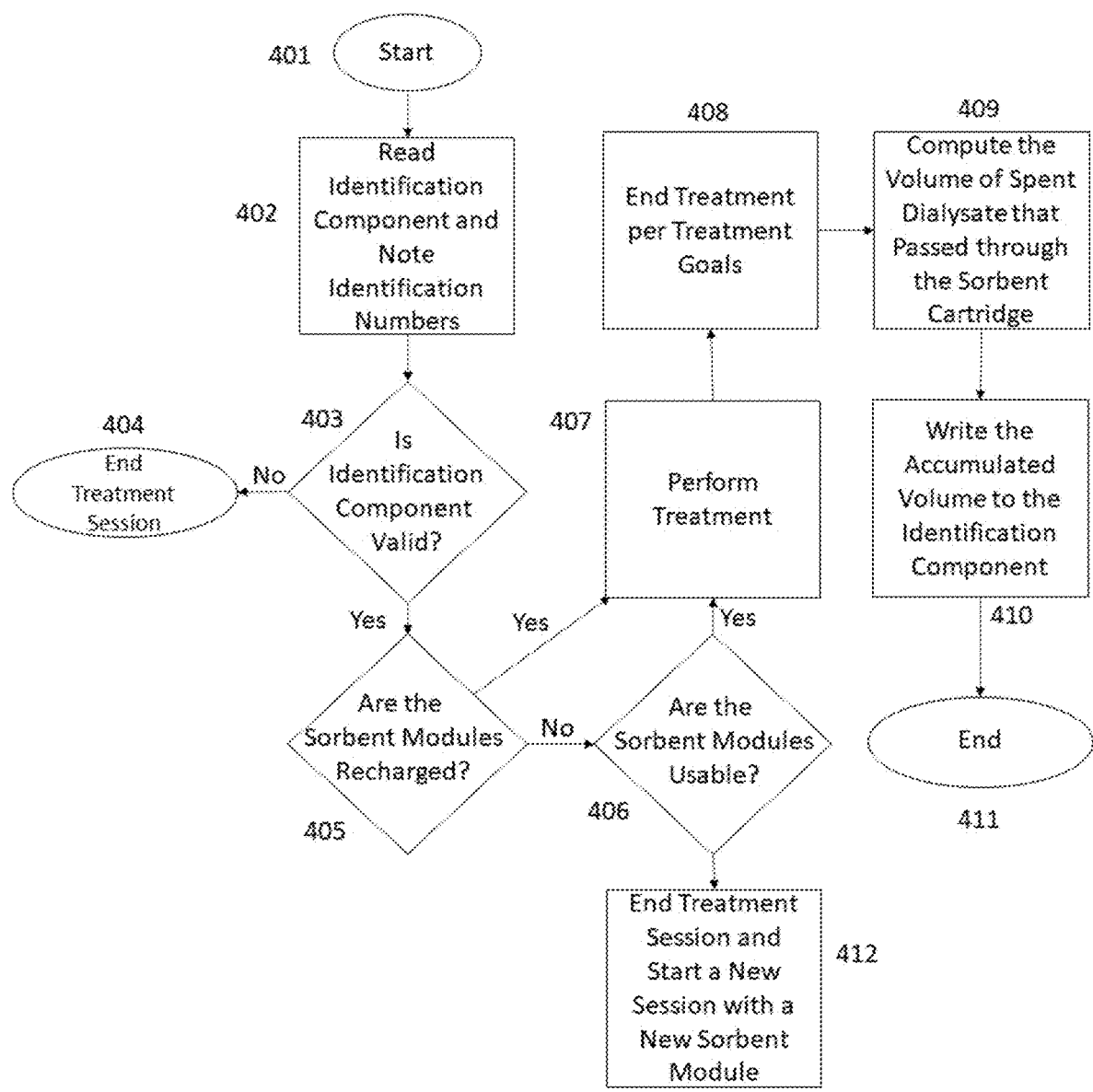
FIG. 5 is a flow chart illustrating a method of using a sorbent module for the second or subsequent time.

FIG. 5 is a flow chart showing the method for using a sorbent module when the sorbent module has been used previously. The method can start in step 401. In step 402, the system can read an identification component attached to or embedded in the sorbent module. In step 403, the system can determine whether the identification component is a valid identification component. If not, the dialysis session can end in step 404. If so, the method continues to step 405. The system can perform the steps of reading the identification component and determining whether the identification component is valid, shown as steps 301 through 304 in FIG. 4 and steps 401 through 404 in FIG. 5, each time the system is used.

If the sorbent module having a valid identification component has been used previously, the system can determine whether the sorbent module was recharged after the prior dialysis session in step 405. Data regarding the last recharge of a sorbent module can be written on the identification component. If the sorbent module has been recharged after the prior dialysis session, then the remaining capacity of the sorbent module should be near 100% and the sorbent module disinfected. As such, treatment can be performed with the sorbent module in step 407. If the sorbent module was not recharged after the previous dialysis session, the system can determine whether the sorbent module is usable in step 406.

As described, the sorbent module can be found usable if the remaining capacity of the sorbent module is enough to perform a dialysis session, and if the bacterial count in the sorbent module is low enough to safely carry out dialysis. The remaining capacity of the sorbent module can be determined based on the volume of dialysate passed through the sorbent cartridge in the previous dialysis session or sessions, which can be obtained from the identification component. The system can determine whether the remaining capacity is above some preset value to allow reuse. The preset value can depend on the goals of the present dialysis session, and in particular, the length of the present dialysis session and the dialysate flow rate to be used. That is, the system can determine if the remaining capacity of the sorbent module allows for reuse at a specified dialysate flow rate and session duration. If a microbe removal layer was used in the previous dialysis session upstream of the sorbent module, then the bacteria and endotoxin levels in the sorbent module should be low after the previous dialysis session. The system can determine if the bacterial and endotoxin levels in the sorbent module remain at a useful level if the prior use of the sorbent module is within a preset length of time. In certain embodiments, the preset length of time can be set for 36 hours. However, shorter durations can be used as the preset length of time to ensure low bacterial levels.

If the system determines that the sorbent module is not useable in step 406, the current dialysis session can be stopped, and the method can begin again using a new sorbent module in step 412. If the sorbent module is determined to be useable, dialysis treatment can begin in step 407. In step 408, the dialysis session can end per the treatment goals. In certain embodiments, the system can prevent treatment or changes in dialysate flow rate if the remaining capacity of the reusable sorbent modules is not enough to support the dialysate flow rate selected by the user. The system can optionally compute the volume of dialysate passed through the sorbent cartridge during the dialysis session in step 409. The accumulated volume passed through the sorbent cartridge since the last recharge, or data that can be used to determine the accumulated volume, can be written to the identification component of each reusable sorbent module in step 410. The method can end in step 411, and the reusable sorbent modules stored or recharged.

One skilled in the art will understand that various combinations and/or modifications and variations can be made in the described systems and methods depending upon the specific needs for operation. Various aspects disclosed herein may be combined in different combinations than the combinations specifically presented in the description and accompanying drawings. Moreover, features illustrated or described as being part of an aspect of the disclosure may be used in the aspect of the disclosure, either alone or in combination, or follow a preferred arrangement of one or more of the described elements. Depending on the example, certain acts or events of any of the processes or methods described herein may be performed in a different sequence, may be added, merged, or left out altogether (e.g., certain described acts or events may not be necessary to carry out the techniques). In addition, while certain aspects of this disclosure are described as performed by a single module or unit for purposes of clarity, the techniques of this disclosure may be performed by a combination of units or modules associated with, for example, a medical device.

What is claimed is:

1. A system, comprising:
   a sorbent module containing at least zirconium oxide and/or zirconium phosphate;
   a microbe removal layer upstream of the sorbent module; and
   a control system programmed to:
   calculate a remaining capacity of the sorbent module following a first dialysis session, wherein the remaining capacity of the sorbent module following the first dialysis session is a function of at least a weight of a patient;
   calculate an estimated capacity of the sorbent module that would be required for a second dialysis session, wherein the second dialysis session would follow the first dialysis session; and
   determine if the sorbent module can be reused for the second dialysis session, without recharging the sorbent module, based on the remaining capacity of the sorbent module and the capacity of the sorbent module required for the second dialysis session,
   wherein the capacity of the sorbent module required for the second dialysis session is based on at least an expected dialysate flow rate through the sorbent module for the second dialysis session and expected duration of the second dialysis session.

2. The system of claim 1, wherein the microbe removal layer is either silver impregnated activated carbon or a halide resin and silver impregnated activated carbon.

3. The system of claim 1, wherein the sorbent module contains zirconium oxide.

4. The system of claim 1, wherein the sorbent module contains zirconium phosphate.

5. The system of claim 1, further comprising an identification component affixed to or embedded in the sorbent module.

6. The system of claim 5, wherein the identification component is an RFID component.

7. The system of claim 5, wherein the control system is programmed to determine whether the sorbent module is usable in a present dialysis session based on data from the identification component.

8. The system of claim 7, wherein the control system is programmed to determine that the sorbent module is usable if the remaining capacity of the sorbent module is above a preset value and either of:
   a) the sorbent module has not been used in a dialysis session since a last recharge; or
   b) the sorbent module has been used in a prior dialysis session since the last recharge and the prior dialysis session was within a preset length of time of the present dialysis session.

9. The system of claim 8, wherein the preset length of time is about 36 hours.

10. The system of claim 8, wherein the remaining capacity of the sorbent module is determined based on a volume of dialysate passed through the sorbent module in the prior dialysis session.

11. A method, comprising the steps of:
    determining whether a first sorbent module containing zirconium oxide and/or zirconium phosphate is useable in a present dialysis session; wherein the first sorbent module was used in a prior dialysis session; and wherein during the prior dialysis session, a microbe removal layer was upstream of the zirconium oxide and/or zirconium phosphate;
    calculating, by a control system, a remaining capacity of the first sorbent module following the prior dialysis session, wherein the remaining capacity of the first sorbent module following the prior dialysis session is a function of at least a weight of a patient;
    calculating, by the control system, an estimated capacity of the first sorbent module that would be required for the present dialysis session, wherein the present dialysis session would follow the prior dialysis session; and
    determining, by the control system, if the first sorbent module can be reused for the present dialysis session, without recharging the first sorbent module, based on the remaining capacity of the first sorbent module and the capacity of the first sorbent module required for the present dialysis session,
    wherein the capacity of the first sorbent module required for the present dialysis session is based on at least an expected dialysate flow rate through the first sorbent module for the present dialysis session and expected duration of the present dialysis session.

12. The method of claim 11, wherein the first sorbent module is determined to be useable if the remaining capacity of the first module is above a preset value and if either:
  a) the first sorbent module has not been used in the dialysis session since a last recharge; or
  b) the first sorbent module has been used in the prior dialysis session since the last recharge and the prior dialysis session was within a preset length of time of the present dialysis session.

13. The method of claim 12, wherein data used to determine whether the first sorbent module is usable is obtained from an identification component affixed to or embedded in the first sorbent module.

14. The method of claim 11, wherein the microbe removal layer is either silver impregnated activated carbon or a halide resin and silver impregnated activated carbon.

15. The method of claim 11, wherein the first sorbent module contains zirconium oxide.

16. The method of claim 11, wherein the first sorbent module contains zirconium phosphate.

17. The method of claim 11, wherein the microbe removal layer was in a second sorbent module.

18. The method of claim 11, wherein the step of determining whether the first sorbent module is usable is performed by a control system of a dialysis system.

19. The method of claim 11, further comprising the step of performing dialysis with the first sorbent module if the first sorbent module is determined to be usable.

* * * * *